US008383350B1

(12) United States Patent
Kolz et al.

(10) Patent No.: US 8,383,350 B1
(45) Date of Patent: Feb. 26, 2013

(54) ASSAY FOR DETECTION OF IL-10 ANTIBODIES

(75) Inventors: Karen Kolz, Union, NJ (US); Constance M. Cullen, Park Ridge, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1335 days.

(21) Appl. No.: 11/960,517

(22) Filed: Dec. 19, 2007

Related U.S. Application Data

(60) Provisional application No. 60/871,063, filed on Dec. 20, 2006.

(51) Int. Cl.
*G01N 33/53* (2006.01)
(52) U.S. Cl. .......................................... 435/7.1; 436/512
(58) Field of Classification Search ........................ None
See application file for complete search history.

(56) References Cited

U.S. PATENT DOCUMENTS

2002/0142356 A1  10/2002  Scalice et al.

OTHER PUBLICATIONS

Baral et al. (2001) *International J of Cancer* 92(1) 88-95 "Murine Monoclonal Anti-idiotypic Antibody as a Surrogate Antigen for Human HER-2/NEU".
Becker et al. (1996) *J. of Immunol. Methods*, 192 (1-2):73-85 "An alternative ELISA for T4 determination based on idiotype anti-idiotype interaction and a latex method for anti-idiotype monoclonal antibody selection".
D'Andrea et al. (1993) *J. Exp. Med.* 178(3):1041 "Interleukin 10 (IL-10) inhibits human lymphcyte interferon γ-production by suppressing natural killer cell stimulatory factor/IL-12 synthesis in accessory cells".
De Waal Malefyt et al. (1991) *J. Exp. Med.* 174(4):915 "Interleukin 10 (IL-10) and Viral IL-10 strongly reduce antigen-specific human T cell proliferation by diminishing the anti-gen-presenting capacity of monocytes via downregulation of class II major histocompatibility complex expression".
Fiorentino et al. (1989) *J. Exp. Med.* 170(6):2081-2095 "Two types of mouse T helper cell, IV. Th2 clones secrete a factor that inhibits cytokine production by Th1 clones".
Fiorentino et al. (1991) *J. Immunol.* 146:3444 "IL-10 acts on the antigen-presenting cell to inhibit cytokine production by Th1 cells".
Fiorentino et al. (1991) *J. Immunol.* 147:3815 "IL-10 inhibits cytokine production by activated macrophages".
Gonzalez-Amaro et al. (1998) *J. Autoimmunity* 11:395-402 "Role of IL-10 in the abnormalities of early cell activation events of lymphocytes from patients with systemic lupus erythematosus".
Hsu et al. (1992) *Int. Immunol.* 4(5):563 "Differential effects of IL-4 and IL-10 on IL-2-induced IFN-γ synthesis and lymphokine-activated killer activity".
Joosten et al. (1997) *Arthritis Rheum.* 40:249-60 "Role of interleukin-4 and interleukin-10 in murine collagen-induced arthritis".
Kohen et al. (2000) *Food and Agriculture Immunology* 12(3):193-201 "Generation of an anti-idiotypic antibody as a surrogate ligand for sulfamethazine in immunoassay procedures".
Losman et al. (1995) *Cancer Research* 55(23 suppl S):S5978-S5982 "Development and evaluation of the specificity of a rat monoclonal anti-idiotype antibody, WN, to an anti-B-cell lymphoma monoclonal antibody, LL2".
Moore et al. (1993) *Annu. Rev. Immunol.* 11:165 "Interleukin-10".

*Primary Examiner* — Prema Mertz
(74) *Attorney, Agent, or Firm* — Sheela Mohan-Peterson

(57) ABSTRACT

Provided are assays to measure the presence and quantity of an antibody of interest in a patient's bloodstream or other biological sample. ECL and ELISA methods, and kits for such assays, as well as anti-idiotypic antibodies provided to detect levels of the antibody in biological samples, which are from, for example, animal models and human patients.

16 Claims, 2 Drawing Sheets

```
                           10                  20
11F12  MDFQVQIFSFLLISASVIMSRG  QIVLTQSPAIMSASLGERVAMTC  TASSSVSSHYLH
13G4   MDFHVQIFSFMLISVTVILSSG  EIVLTQSPALMAASPGEKVTITC  SVSSSISSSKLY
                                                        ----CDRL1---
                                             40
       WYQQKPGSSPKLWIY
       WYQQKSETSPKPWIY
       --

50              60              70              80
       STSNLAS  GVPARFSGSGSGTSYSLTIS  SMEAEDAATYYC
       GTSNLAS  GVPVRFSGSGSGTSYSLTIS  SMEAEDAATYYC
       --CDRL2-

90             100
       HQYHRSPWT  FGGGTKLEIKR
       QQWSSYPLT  FGAGTKLELKR
       --CDRL3--

11F12 Variable Light Chain - SEQ ID NO: 2
13G4  Variable Light Chain - SEQ ID NO: 4
```

FIGURE 2

SEQUENCE LISTING

```
<160> NUMBER OF SEQ ID NOS: 4

<210> SEQ ID NO 1
<211> LENGTH: 136
<212> TYPE: PRT
<213> ORGANISM: Mus musculus
<220> FEATURE:
<221> NAME/KEY: SIGNAL
<222> LOCATION: (1)..(19)
<220> FEATURE:
<221> NAME/KEY: MISC_FEATURE
<222> LOCATION: (45)..(54)
<223> OTHER INFORMATION: VH CDR1
<220> FEATURE:
<221> NAME/KEY: MISC_FEATURE
<222> LOCATION: (69)..(85)
<223> OTHER INFORMATION: VH CDR2
<220> FEATURE:
<221> NAME/KEY: MISC_FEATURE
<222> LOCATION: (118)..(126)
<223> OTHER INFORMATION: VH CDR3
```

-continued

<400> SEQUENCE: 1

Met Gly Trp Thr Trp Ile Phe Leu Phe Leu Ser Gly Thr Ala Gly
1               5                   10                  15

Val His Ser Glu Val Gln Val Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Lys Thr Leu
    50                  55                  60

Glu Trp Ile Gly Leu Ile Asn Pro Tyr Asn Gly Gly Thr Thr Tyr Asn
65              70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Arg Gly Ser Gly Tyr Ala Met Asp Tyr Trp Gly
        115                 120                 125

Gln Gly Thr Ser Val Thr Val Ser
    130                 135

<210> SEQ ID NO 2
<211> LENGTH: 131
<212> TYPE: PRT
<213> ORGANISM: Mus musculus
<220> FEATURE:
<221> NAME/KEY: SIGNAL
<222> LOCATION: (1)..(22)
<220> FEATURE:
<221> NAME/KEY: MISC_FEATURE
<222> LOCATION: (46)..(57)
<223> OTHER INFORMATION: VL CDR1
<220> FEATURE:
<221> NAME/KEY: MISC_FEATURE
<222> LOCATION: (73)..(79)
<223> OTHER INFORMATION: VL CDR2
<220> FEATURE:
<221> NAME/KEY: MISC_FEATURE
<222> LOCATION: (112)..(120)
<223> OTHER INFORMATION: VL CDR3

<400> SEQUENCE: 2

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Leu Gly Glu Arg Val Ala Met Thr Cys Thr Ala Ser
        35                  40                  45

Ser Ser Val Ser Ser His Tyr Leu His Trp Tyr Gln Gln Lys Pro Gly
    50                  55                  60

Ser Ser Pro Lys Leu Trp Ile Tyr Ser Thr Ser Asn Leu Ala Ser Gly
65              70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys His
            100                 105                 110

Gln Tyr His Arg Ser Pro Trp Thr Phe Gly Gly Gly Thr Lys Leu Glu
        115                 120                 125

Ile Lys Arg
130

```
<210> SEQ ID NO 3
<211> LENGTH: 136
<212> TYPE: PRT
<213> ORGANISM: Mus musculus
<220> FEATURE:
<221> NAME/KEY: SIGNAL
<222> LOCATION: (1)..(19)
<220> FEATURE:
<221> NAME/KEY: MISC_FEATURE
<222> LOCATION: (45)..(54)
<223> OTHER INFORMATION: VH CDR1
<220> FEATURE:
<221> NAME/KEY: MISC_FEATURE
<222> LOCATION: (69)..(85)
<223> OTHER INFORMATION: VH CDR2
<220> FEATURE:
<221> NAME/KEY: MISC_FEATURE
<222> LOCATION: (118)..(126)
<223> OTHER INFORMATION: VH CDR3

<400> SEQUENCE: 3
```

Met Asn Phe Gly Leu Ser Leu Ile Phe Leu Val Leu Ile Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Ala Phe
        35                  40                  45

Ser Ser Tyr Asp Met Ser Trp Val Arg Gln Thr Pro Glu Lys Arg Leu
    50                  55                  60

Glu Trp Val Ala Ser Ile Ser Ser Asp Gly Ser Tyr Thr Tyr Tyr Pro
65                  70                  75                  80

Asp Thr Val Lys Gly Arg Phe Thr Ile Ser Arg Asp Asn Ala Arg Asn
                85                  90                  95

Thr Leu Asn Leu Gln Met Ser Ser Leu Arg Ser Glu Asp Thr Ala Leu
            100                 105                 110

Tyr Phe Cys Ala Arg Gln Asp Gly Tyr Tyr Leu Asp Tyr Trp Gly Gln
        115                 120                 125

Gly Thr Thr Leu Thr Val Ser Ser
    130                 135

```
<210> SEQ ID NO 4
<211> LENGTH: 131
<212> TYPE: PRT
<213> ORGANISM: Mus musculus
<220> FEATURE:
<221> NAME/KEY: SIGNAL
<222> LOCATION: (1)..(22)
<220> FEATURE:
<221> NAME/KEY: MISC_FEATURE
<222> LOCATION: (46)..(57)
<223> OTHER INFORMATION: VL CDR1
<220> FEATURE:
<221> NAME/KEY: MISC_FEATURE
<222> LOCATION: (73)..(79)
<223> OTHER INFORMATION: VL CDR2
<220> FEATURE:
<221> NAME/KEY: MISC_FEATURE
<222> LOCATION: (102)..(110)
<223> OTHER INFORMATION: VL CDR3
<220> FEATURE:
<221> NAME/KEY: MISC_FEATURE
<222> LOCATION: (112)..(120)
<223> OTHER INFORMATION: VL CDR3

<400> SEQUENCE: 4
```

Met Asp Phe His Val Gln Ile Phe Ser Phe Met Leu Ile Ser Val Thr
1               5                   10                  15

Val Ile Leu Ser Ser Gly Glu Ile Val Leu Thr Gln Ser Pro Ala Leu

-continued

```
             20                  25                  30
Met Ala Ala Ser Pro Gly Glu Lys Val Thr Ile Thr Cys Ser Val Ser
        35                  40                  45

Ser Ser Ile Ser Ser Ser Lys Leu Tyr Trp Tyr Gln Gln Lys Ser Glu
        50                  55                  60

Thr Ser Pro Lys Pro Trp Ile Tyr Gly Thr Ser Asn Leu Ala Ser Gly
65                      70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Gln Trp Ser Ser Tyr Pro Leu Thr Phe Gly Ala Gly Thr Lys Leu Glu
        115                 120                 125

Leu Lys Arg
130
```

ASSAY FOR DETECTION OF IL-10 ANTIBODIES

This filing is a U.S. Patent Application which claims benefit of U.S. Provisional Patent Application No. 60/871,063, filed Dec. 20, 2006, which is incorporated herein by reference.

FIELD OF THE INVENTION

The present invention relates to a high-throughput assay based on use of anti-idiotypic antibodies for detecting antibodies to soluble immune factors, such as for quantitating humanized anti-IL-10 antibody in serum for clinical studies.

BACKGROUND OF THE INVENTION

Initially known as cytokine synthesis inhibitor factor or CSIF, interleukin-10 (IL-10) is a potent immunomodulator of hematopoietic cells, particularly immune cells. Cells such as activated Th2 cells, B cells, keratinocytes, monocytes and macrophages produce IL-10. See, e.g., Moore et al., *Annu. Rev. Immunol.* 11:165 (1993). IL-10 inhibits activation and effector functions of a number of cells that include T cells, monocytes and macrophages. In particular, IL-10 inhibits cytokine synthesis, including that of IL-1, IFN-γ, and TNF, by cells such as Th1 cells, natural killer cells, monocytes, and macrophages. See, e.g., Fiorentino et al., *J. Exp. Med.,* 170:2081-2095 (1989); Fiorentino et al., *J. Immunol.* 146:3444 (1991); Hsu et al., *Int. Immunol.* 4:563 (1992); Hsu et al., *Int. Immunol.* 4:563 (1992); D'Andrea et al., *J. Exp. Med.* 178:1041 (1993); de Waal Malefyt et al., *J. Exp. Med.* 174:915 (1991); Fiorentino et al., *J. Immunol.* 147:3815 (1991).

Multiple pathogens, particularly intracellular pathogens, elicit IL-10 production to slow or completely stall the effective removal of the pathogen by the immune response. Moore et al., *Annu. Rev. Immunol.* 11:165 (1993). For example, in blood lymphocytes from patients with HIV, leprosy, or tuberculosis, peripheral blood lymphocytes are typically anergic or nonresponsive in vitro when challenged with the pathogen. However, the neutralization of IL-10 in these demonstrated that an active effector response, i.e., Th1 reactivity, was present in these cells. Thus, it is believed that IL-10 is effectively commandeered by the pathogen to facilitate its infective state.

IL-10 is also associated with autoimmunity in vivo. Autoimmunity results from the development from autoantibodies, autoreactive T cells, or some combination thereof that target normal tissue. One example of autoimmune disease is systemic lupus erythematosus (SLE), a chronic rheumatic disease in which connective tissue throughout the body becomes inflamed. Autoantibodies that attack normal body tissue as if it were an outside invade result in the characteristic inflammation. While the precise cause is not fully understood, researchers believe it has both genetic and environmental components. Specifically, B-cell hyperactivity and the presence of various autoantibodies characterize SLE. Typically, IgG autoantibodies reactive to double stranded DNA (IgG anti-dsDNA abs) are elevated in patients with SLE. Between 60 and 70% of SLE patients produce IgG anti-dsDNA abs, some of which are nephrotoxic. SLE is ten times more prevalent in women than men, with symptoms ranging from facial rashes to disabling and potentially life-threatening organ dysfunction. It can develop at any age, but is most common in young adults.

Numerous studies support a role for IL-10 in the pathology associated with SLE. For example, while IL-10 is typically not produced by cells without appropriate stimulation, both B cells and macrophages from SLE patients spontaneously produce high levels of IL-10 in vitro. Llorente, et al., *Arthritis Rheum.* 40:249-60 (1997). In several studies, researchers demonstrated a correlation between serum levels of IL-10 and disease activity. Moreover, both in vivo and in vitro studies demonstrated that the blockade of IL-10 production can alleviate the clinical manifestations of SLE. See, e.g., Gonzalez-Amaro, et al. *J. Autoimmunity* 11:395-402 (1998).

Typically, immunoassays for high-concentration, high-molecular-weight analytes in the marketplace are predicated on the multivalence of the analyte. Ultimately, the analyte is detected by some sort of cross-linking, either by agglutination (in turbidimetric or nephelometric assays), precipitation (radial immunodiffusion), or sandwich immunoassays such as ELISAs.

U.S. Pub. No. US 2002/0142356 provides a method for obtaining anti-idiotypic monoclonal antibody populations directed to an antibody that is specific for a high-concentration, high-molecular-weight target antigen wherein said anti-idiotypic antibody populations have a wide range of binding affinities for the selected antibody specific to said target antigen and wherein a subset of said anti-idiotypic antibody populations can be selected having the required affinity for a particular application. U.S. Pub. No. US 20020142356 involves a competitive immunoassay of an antigen using an antibody as coat and an anti-idiotypic antibody as detection or vice-versa. Other references disclosing use of an anti-idiotypic antibody as a surrogate antigen include Losman, *Cancer Research,* 55 (23 suppl S):S5978-S5982 (1995); Becker, *J. of Immunol. Methods,* 192 (1-2):73-85 (1996); Baral, *International J of Cancer,* 92(1) 88-95 (2001); and Kohen, *Food and Agriculture Immunology,* 12(3):193-201 (2000).

There exists a need to detect humanized antibodies to cytokines such as IL-10 in biological samples without also detecting certain other antibodies directed or not directed to such proteins, particularly in clinical samples. The present invention fulfills this need by providing anti-idiotypic antibodies against humanized anti-IL-10 used in a detection assay to monitor levels of the humanized antibody in biological samples.

BRIEF DESCRIPTION OF THE DRAWINGS

FIG. 2 shows an alignment of humanized 12G8 anti-idiotypic antibodies, 11F12 and 13G4, variable light chain domains (SEQ ID NOs: 2 and 4, respectively). CDRL1, CDRL2, and CDRL3 are designated. The signal sequence is underlined.

SUMMARY OF THE INVENTION

Figure 1:
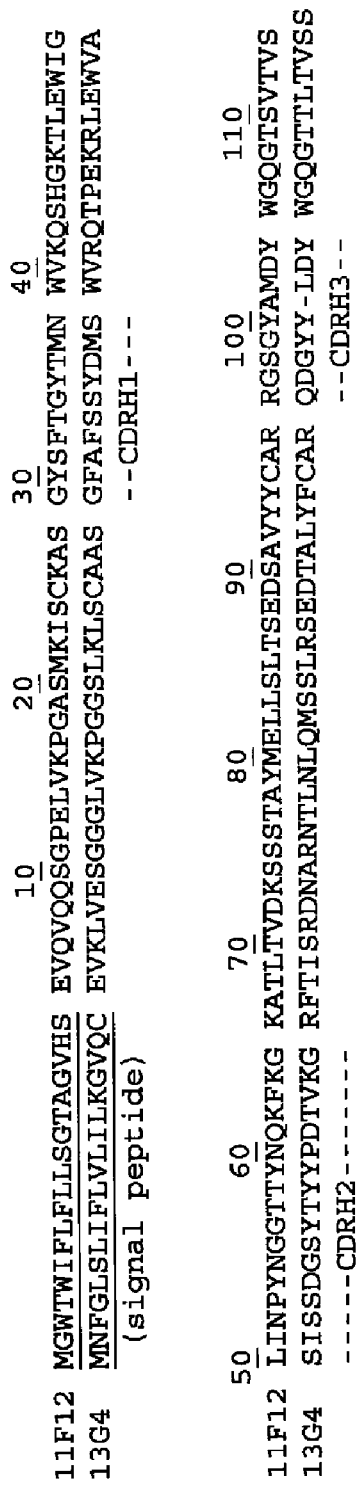
FIG. 1 shows an alignment of humanized 12G8 anti-idiotypic antibodies, 11F12 and 13G4, variable heavy chain domains (SEQ ID NOs 1 and 3, respectively). CDRH1, CDRH2, and CDRH3 are designated. The signal sequence is underlined.

The present invention provides an assay method for specifically detecting in a biological sample an antibody of interest that binds to mammalian IL-10 comprising (a) contacting and incubating the biological sample with a first idiotypic antibody, which binds to the antibody of interest but not any other antibody in the sample that binds to mammalian IL-10; (b) contacting the sample, and hence any bound antibody of interest, with a second idiotypic antibody which binds to the antibody of interest but not any other antibody in the sample that binds to mammalian IL-10; and (c) measuring the level of any of the antibody of interest bound. The antibody of interest can be a monoclonal antibody, or in certain embodiments, a humanized antibody. The detectable antibody is a detectable anti-idiotypic antibody binding to the idiotype of the antibody of interest but not to the idiotype of at least one other antibody in the sample that binds to mammalian IL-10. The biological sample can be isolated from a primate subject, including a cynomologous monkey or a human. In a further embodiment, the method of claim 1 wherein the measuring step further comprises using a standard curve to determine the level of the antibody of interest compared to a known level. The biological sample can be plasma, serum, or urine. The mammalian IL-10 is primate IL-10, including cynomologous monkey and human IL-10. In one embodiment, the antibody of interest is a humanized 12G8 antibody. The first and second idiotypic antibodies are monoclonal antibodies. In a further embodiment the first and second idiotypic antibodies are murine antibodies. The first idiotypic antibody is a capture reagent selected from the group consisting of 11F12 and 13G4, where 11F12 and 13G4 have variable heavy chain sequences as shown in FIG. 1, and 11F12 and 13G4 have variable light chain sequences as shown in FIG. 2. The capture reagent and detectable antibody can be the same or may be different In one embodiment the assay is an electrochemiluminescence (ECL) immunoassay and 11F12 is the capture reagent and 13G4 is the detectable antibody. 11F12 may be conjugated to biotin and 13G4 may be conjugated to ruthenium. In another embodiment, the assay is an enzyme-linked immunosorbent assay (ELISA) and 13G4 is the capture reagent and 11F12 is the detectable antibody. 11F12 can be conjugated to biotin.

Also encompassed by the present invention is an ELISA kit for specifically detecting in a biological sample an antibody of interest that binds to a a mammalian IL-10, the kit comprising: (a) a container containing, as a capture reagent, an anti-idiotypic antibody binding to the idiotype of the antibody of interest but not to the idiotype of at least one other antibody in the sample that binds to the protein; (b) a container containing a detectable anti-idiotypic antibody that binds to the idiotype of the antibody of interest but not to the idiotype of at least one other antibody in the sample that binds to the protein; and (c) instructions for detecting said antibody of interest.

Also provided is a solid support for the capture reagent. The capture reagent can be immobilized on the solid support. In certain embodiments the solid support is a microtiter plate. It is further contemplated that the kit provides a detection means for the detectable antibody. The detection means can be avidin or streptavidin-horseradish peroxidase. It is also contemplated that the kit also contains the purified antibody of interest as a standard.

In one embodiment the capture reagent and detectable antibody are monoclonal antibodies. In one embodiment, 11F12 is the capture reagent, and 13G4 is the detection antibody.

The present invention also provides an ECL immunoassay kit for specifically detecting in a biological sample an antibody of interest that binds to a mammalian IL-10, the kit comprising: (a) a container containing, as a capture reagent, a first anti-idiotypic antibody binding to the idiotype of the antibody of interest but not to the idiotype of at least one other antibody in the sample that binds to the protein; (b) a container containing a detectable anti-idiotypic antibody that binds to the idiotype of the antibody of interest but not to the idiotype of at least one other antibody in the sample that binds to the protein; and (c) instructions for detecting said antibody of interest. In one embodiment, the capture reagent and detectable antibody are the same. In a second embodiment, the capture reagent and detectable antibody are different. In yet another embodiment, 11F12 is the capture reagent and 13G4 is the detectable antibody. 11F12 is conjugated to biotin and 13G4 is conjugated to ruthenium. The antibody of interest is a humanized antibody, in particular a humanized 12G8 antibody.

DETAILED DESCRIPTION

I. Definitions

Mammal" for purposes of treatment refers to any animal classified as a mammal, including humans, domestic, and farm animals, and zoo, sports, or pet animals, such as dogs, horses, cats, sheep, pigs, cows, etc. In certain embodiments, the mammal is a primate including cynomologous monkey and human.

The term "detecting" is used in the broadest sense to include both qualitative and quantitative measurements of a target molecule. In one aspect, the detecting method as described herein is used to identify the mere presence of the antibody of interest in a biological sample. In another aspect, the method is used to test whether the antibody of interest in a sample is present at a detectable level. In yet another aspect, the method can be used to quantify the amount of the antibody of interest in a sample and further to compare the antibody levels from different samples.

The term "antibody of interest" refers to an antibody that binds to a protein as described herein. Such an antibody is a monoclonal antibody, in particular, a rodent, e.g., murine antibody or a humanized antibody. Examples of such antibodies include an antibody or functional fragment thereof that binds to a mammalian IL-10, including primate IL-10. In certain embodiments, the IL-10 is from a cynomologous monkey or human. In the present invention, the antibody of interest is humanized 12G8 as described in US2005/0101770.

The term "biological sample" refers to any biological substance that may contain the antibody of interest. A sample can be biological fluid, such as whole blood or whole blood components including red blood cells, white blood cells, platelets, serum and plasma, ascites, urine, vitreous fluid, lymph fluid, synovial fluid, follicular fluid, seminal fluid, amniotic fluid, milk, saliva, sputum, tears, perspiration, mucus, cerebrospinal fluid, and other constituents of the body that may contain the analyte of interest, as well as tissue culture medium and tissue extracts such as homogenized tissue, and cellular extracts. Preferably, the sample is a body sample from any animal, but preferably is from a mammal, more preferably from a primate subject, for example, a cynomologous monkey or human when measuring an antibody such as a humanized antibody in a clinical sample. Such biological sample is from clinical patient and can be serum, plasma or urine.

The term "capture reagent" or "coat antibody" refers to an anti-idiotypic antibody or mixture of such antibodies that bind an idiotype of the antibody of interest and are capable of binding and capturing the antibody of interest in a biological sample such that under suitable conditions, the complex of capture reagent and antibody of interest can be separated from the rest of the sample.

An anti-idiotypic (anti-Id) antibody is an antibody which recognizes unique determinants generally associated with the antigen-binding site of an antibody. Anti-idiotypic typically bind to the $V_H$ and/or $V_L$ domain of the cognate antibody, in this case the antibody of interest. Typically, such anti-idiotypic antibodies are prepared by immunizing a mammal such as a mouse with the antibody of interest. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference. Antibodies that give the cleanest signal in an assay, whether for the capture reagent or the detectable antibody are selected from a hybridoma produced with spleen cells from the immunized animal. Typically for ELISA based assays, the capture reagent is immobilized or immobilizable, whereas ECL based immunoassays do not require immobilization. Such anti-idiotypic antibodies are monoclonal antibodies, rodent antibodies, e.g., murine or rat antibodies.

The term "detectable antibody" refers to an anti-idiotypic antibody or mixture of such antibodies that bind an idiotype of the antibody of interest and are capable of being detected either directly through a label amplified by a detection means, or indirectly through, e.g., another antibody that is labeled. For direct labeling, the antibody is typically conjugated to a moiety that is detectable by some means, e.g., biotin or ruthenium. Such anti-idiotypic antibodies are monoclonal antibodies, including rodent antibodies, e.g., murine or rat antibodies.

The terms "label" or "detectable label" is any chemical group or moiety that can be linked to the target substance. In one embodiment of the invention, the label is a detectable label that is suitable for the sensitive detection of the target substance. Examples of detectable labels include luminescent labels (e.g., fluorescent, phosphorescent, chemiluminescent, bioluminescent and electrochemiluminescent labels), radioactive labels, enzymes, particles, magnetic substances, electroactive species and the like. Alternatively, a detectable label may signal its presence by participating in specific binding reaction. Examples of such labels include haptens, antibodies, biotin, streptavidin, his-tag, nitrilotriacetic acid, glutathione S-transferase, glutathione and the like.

The term "detection means" refers to a moiety or technique used to detect the presence of the detectable antibody through signal reporting that is then read out in the assay herein. It can reagents that amplify the immobilized label such as the label captured onto a microtiter plate, e.g., avidin or streptavidin-HRP.

"Photoluminescence" is the process whereby a material luminesces subsequent to the absorption by that material of light (alternatively termed electromagnetic radiation or emr). Fluorescence and phosphorescence are two different types of photoluminescence. "Chemiluminescent" processes entail the creation of the luminescent species by a chemical reaction. "Electro-chemiluminescence" or "ECL" is the process whereby a species, e.g., antibody of interest, luminesces upon the exposure of that species to electrochemical energy in an appropriate surrounding chemical environment.

Herein, the term "ECL moiety", "metal-containing ECL moiety" "label", "label compound", and "label substance", are used interchangeably. It is within the scope of the invention for the species termed "ECL moiety", "metal-containing ECL moiety", "organometallic", "metal chelate", "transition metal chelate" "rare earth metal chelate", "label compound", "label substance" and "label" to be linked to other molecules such as an antibody or an antibody fragment thereof. The above-mentioned species can also be linked to a combination of one or more binding partners and/or one or more reactive components. Additionally, the aforementioned species can also be linked to an antibody or an antibody fragment thereof bound to a binding partner, a reactive component, or a combination of one or more binding partners and/or one or more reactive components. It is also within the scope of the invention for a plurality of the aforementioned species to be bound directly, or through other molecules as discussed above, to an antibody or antibody fragment thereof.

As used herein, the term "antibody" refers to any form of antibody or fragment thereof that exhibits the desired activity. Thus, it is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

Therefore, the term "antibody fragment" or "binding fragment" refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of the full length antibody's activity. Preferably, a binding fragment or derivative retains at least 25%, 50%, 60%, 70%, 80%, 90%, 95%, 99% or 100% (or more) of the full length antibody's activity, although any binding fragment with sufficient affinity to exert the desired biological effect will be useful. It is also intended that an antibody fragment or binding fragment can include conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al., (1991) *Nature* 352: 624-628 and Marks et al., (1991) *J. Mol. Biol.* 222: 581-597, for example.

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079, which are hereby incorporated by reference in their entireties). In one embodiment, the present invention provides single domain antibodies comprising two $V_H$ domains with modifications such that single domain antibodies are formed.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum" is added to antibody clone designations when necessary to distinguish humanized antibodies (e.g. hum12G8) from parental rodent antibodies (e.g. rat or mouse 12G8, or "m12G8"). The humanized forms of rodent antibodies will generally comprise the same CDR sequences of the parental rodent antibodies, although certain amino acid substitutions may be included to increase affinity or increase stability of the humanized antibody.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al., (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing.

II. General

The present invention is based upon the development of drug level assays to test for the presence of a humanized cytokine antibody in a biological sample. The assays involve the use of two anti-idiotypic antibodies raised against the humanized cytokine antibody. Sequences of the variable heavy chains of 11F12 and 13G4 (SEQ ID NOs: 1 and 3) are shown in FIG. 1. Corresponding sequences of the variable light chains of 11F12 and 13G4 (SEQ ID NOs: 2 and 4) are shown in FIG. 2. The humanized cytokine antibody is a humanized anti-IL-10 antibody, designated 12G8. See, e.g., US2005/0101770, which is incorporated by reference, for a full description of humanized 12G8 antibody.

III. Assays

The assay described herein can be an electrochemiluminescence (ECL) or enzyme-linked immunosorbent assay (ELISA) that utilizes anti-idiotypic antibodies as capture reagents and detection antibodies for an antibody of interest. In the ECL, one anti-idiotypic antibody is labeled, e.g., biotin, and a second anti-idiotypic antibody is labeled with a second distinct label, e.g., ruthenium. The ELISA is cell-based with a capture reagent as a first anti-idiotypic antibody which attached to a solid substrate, and a second anti-idiotypic antibody that is detectably labeled.

Electrochemiluminescent (ECL) assay techniques are an improvement on chemiluminescent techniques. They provide a sensitive and precise measurement of the presence and concentration of an analyte of interest. In such techniques, the incubated sample is exposed to a voltammetric working electrode in order to trigger luminescence. In the proper chemical environment, such electrochemiluminescence is triggered by a voltage impressed on the working electrode at a particular time and in a particular manner. The light produced by the label is measured and indicates the presence or quantity of the analyte. For a description of such ECL techniques, see, e.g., U.S. Pat. No. 5,238,808 and WO86/0273, each of which is incorporated by reference.

Additionally, although the emission of visible light is an advantageous feature of certain embodiments of the invention it is within the scope of the invention for the composition or system to emit other types of electromagnetic radiation, such as infrared or ultraviolet light, X-rays, microwaves, etc. Use of the terms "electrochemiluminescence", "electrochemiluminescent" "electrochemiluininesce" "luminescence", "luminescent", and "luminesce" in connection with the present invention does not require that the emission be light, but admits of the emission's being such other forms of electromagnetic radiation.

Typically, the analyte of interest is present at a concentration of $10^{-3}$ molar or less, for example, at least as low as $10^{-18}$ molar.

An essential feature of the invention is the utilization of metal-containing ECL moieties which are capable of electrochemiluminescence (ECL). These encompass organometallic compounds which luminesce, such as 4,4',5',5 tetramethyl bipyridine Re(I)(4-ethyl pyridine)(CO)$_3$$^+$CF$_3$SO$_3$$^-$; and Pt2-(2-thienyl)$_2$ pyridine.

Advantageously, the ECL moieties are metal chelates. The metal of that chelate is suitably any metal such that the metal chelate will luminesce under the electrochemical conditions which are imposed on the reaction system in question. The metal of such metal chelates is, for instance, a transition metal (such as a d-block transition metal) or a rare earth metal. The metal can be ruthenium, osmium, rhenium, iridium, rhodium, platinum, indium, palladium, molybdenum, technetium, copper, chromium or tungsten.

The ligands which are linked to the metal in such chelates are usually heterocyclic or organic in nature, and play a role in determining whether or not the metal chelate is soluble in an aqueous environment or in an organic or other nonaqueous environment. The ligands can be polydentate, and can be substituted. Polydentate ligands include aromatic and aliphatic ligands. Suitable aromatic polydentate ligands include aromatic heterocyclic ligands. Preferred aromatic heterocyclic ligands are nitrogen-containing, such as, for example, bipyridyl, bipyrazyl, terpyridyl, and phenanthrolyl. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxysuccinimide. The chelate may have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stilbenes, and arsines.

Examples of suitable chelates are bis
[(4,4'-carbomethoxy)-2,2'-bipyridinel]2-[3-(4-methyl-2,2'-bipyridine-4-yl)propyl]-1,3-dioxolane ruthenium (II); bis (2,2' bipyridine)
[4-(butan-1-a1)-4'-methyl-2,2'-bipyridine] ruthenium (II); bis(2,2'-bipyridine).
[4-(4'-methyl-2,2'-bipyridine-4'-yl)-butyric acid] ruthenium (II); (2,2'-bipyridine)
[bis-bis(1,2-diphenylphosphino)ethylene]
2-[3-(4-methyl-2,2'-bipyridine-4'-yl)propyl]-1,3-dioxolane osmium (II); bis(2,2'-bipyridine)
[4-(4'-methyl-2,2'-bipyridine)-butylamine] ruthenium (II); bis(2,2'-bipyridine)
[1-bromo-4(4'-methyl-2,2'-bipyridine-4-yl)butane] ruthenium (II); bis(2,2'-bipyridine)maleimidohexanoic acid,
4-methyl-2,2'-bipyridine-4'-butylamide ruthenium (II).

The function of the ECL moieties in the present invention is to emit electromagnetic radiation as a result of introduction into the reaction system of electrochemical energy. In order to do this, they must be capable of being stimulated to an excited energy state and also capable of emitting electromagnetic radiation, such as a photon of light, upon descending from that excited state. While not wishing to be bound by theoretical analysis of the mechanism of the ECL moiety's participation in the electrochemiluminescent reaction, it is believed that it is oxidized by the introduction of electrochemical energy into the reaction system and then, through interaction with a reductant present in the system, is converted to the excited state. This state is relatively unstable, and the metal chelate quickly descends to a more stable state. In so doing, the chelate gives off electromagnetic radiation, such as a photon of light, which is detectable.

The ECL moiety is linked to at least one substance selected from the group consisting of (i) at least one anti-idiotypic antibody raised against the antibody of interest and (iii) a binding fragment of an anti-idiotypic antibody raised against the antibody of interest.

In order to operate a system in which an electrode introduces electrochemical energy, it is necessary to provide an electrolyte in which the electrode is immersed and which contains the ECL moiety. The electrolyte is a phase through which charge is carried by ions. Generally, the electrolyte is in the liquid phase, and is a solution of one or more salts or other species in water, an organic liquid or mixture of organic liquids, or a mixture of water and one or more organic liquids. However, other forms of electrolyte are also useful in certain embodiments of the invention. For example, the electrolyte may be a dispersion of one or more substances in a fluid—e.g., a liquid, a vapor, or a supercritical fluid, or may be a solution of one or more substances in a solid, a vapor or supercritical fluid.

The electrolyte is suitably a solution of a salt in water. The salt can be a sodium salt or a potassium salt preferably, but incorporation of other cations is also suitable in certain embodiments, as long as the cation does not interfere with the electrochemiluminescent interaction sequence. The salt's anion may be a phosphate, for example, but the use of other anions is also permissible in certain embodiments of the invention—once again, as long as the selected anion does not interfere with the electrochemiluminescent interaction sequence.

The composition may also be nonaqueous. While supercritical fluids can in certain instances be employed advantageously, it is more typical to utilize an electrolyte comprising an organic liquid in a nonaqueous composition. Like an aqueous electrolyte, the nonaqueous electrolyte is also a phase through which charge is carried by ions. Normally, this means that a salt is dissolved in the organic liquid medium. Examples of suitable organic liquids are acetonitrile, dimthylsulfoxide (DMSO), dimethylformamide (DMF), methanol, ethanol, and mixtures of two or more of the foregoing. Illustratively, tetraalkylammonium salts, such as tetrabutylammonium tetrafluoroborate, which are soluble in organic liquids can be used with them to form nonaqueous electrolytes.

The electrolyte is, in certain embodiments of the invention, a buffered system. Phosphate buffers are often advantageous. Examples are an aqueous solution of sodium phosphate/sodium chloride, and an aqueous solution of sodium phosphate/sodium fluoride.

Various assay formats can be employed in the practice of the invention as will be apparent to those skilled in the art. These include a sandwich assay using, for example, magnetic beads or other solid support such as carbon fibrils and a non-competitive assay using a secondary antibody, e.g., idiotypic antibody, that binds to the antibody of interest at an epitope distinct from the first antibody containing the ECL moiety (see, e.g., *The Immunoassay Handbook*, D. Wild, Ed. (1994) Stockton Press, New York).

In another embodiment, described herein is an ELISA that utilizes anti-idiotypic antibodies as capture reagents and detectable antibodies for an antibody of interest. Preferably, the ELISA is cell-based. In the first step of the assay the biological sample suspected of containing or containing the antibody of interest is contacted and incubated with the capture (or coat) antibodies so that the capture antibodies capture or bind to the antibody of interest so that it can be detected in a detection step. The detection step involves use of the detectable anti-idiotypic antibody, which, when contacted with any of the bound antibody of interest, binds to the antibody of interest, if present, and a detection means is used to detect the label on the antibody and hence the presence or amount of antibody of interest present.

The biological sample suspected of containing or containing the antibody of interest is contacted and incubated with the capture (or coat) antibodies so that the capture antibodies capture or bind to the antibody of interest so that it can be detected in a detection step. The detection step involves use of the detectable anti-idiotypic antibody, which, when contacted with any of the bound antibody of interest, binds to the antibody of interest, if present, and a detection means is used to detect the label on the antibody and hence the presence or amount of antibody of interest present.

The solid phase used for immobilization may be any inert support or carrier that is essentially water insoluble and useful in immunometric assays, including supports in the form of, e.g., surfaces, particles, porous matrices, etc. Examples of commonly used supports include small sheets, SEPHADEX® gels, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Alternatively, reactive water-insoluble matrices such as cyanogens-bromide-activated carbohydrates and the reactive substrates described in U.S. Pat. Nos. 3,969,287; 3,691,016; 4,195,128; 4,247,642; 4,229,537; and 4,330,440 are suitably employed for capture-reagent immobilization. In a preferred embodiment, the immobilized capture reagents are coated on a microtiter plate, and in particular the preferred solid phase used is a multi-well microtiter plate that can be used to analyze several samples at one time. The most preferred is a MICROTEST® or MAXISORP® 96-well ELISA plate such as that sold as NUNC MAXISORB® or IMMULON®.

The solid phase is coated with the capture reagents as defined above, which may be linked by a non-covalent or covalent interaction or physical linkage as desired. Techniques for attachment include those described in U.S. Pat. No. 4,376,110 and the references cited therein. If covalent, the plate or other solid phase is incubated with a cross-linking agent together with the capture reagent under conditions well known in the art such as for one hour at room temperature.

Commonly used cross-linking agents for attaching the capture reagents to the solid-phase substrate include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-((p-azidophenyl)-dithio)propioimidate yield photoactivatable intermediates capable of forming cross-links in the presence of light.

If 96-well plates are utilized, they are preferably coated with the mixture of capture reagents typically diluted in a buffer such as 0.05 M sodium carbonate by incubation for at least about 10 hours, more preferably at least overnight, at temperatures of about 4-20° C., more preferably about 4-8° C., and at a pH of about 8-12, more preferably about 9-10, and most preferably about 9.6. If shorter coating times (1-2 hours) are desired, one can use 96-well plates with nitrocellulose filter bottoms (Millipore MULTISCREEN®) or coat at 37° C. The plates may be stacked and coated long in advance of the assay itself, and then the assay can be carried out simultaneously on several samples in a manual, semi-automatic, or automatic fashion, such as by using robotics.

The coated plates are then typically treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, preferably about 1.5 to 3 hours.

After coating and blocking, the standard (purified antibody of interest) or the biological sample to be analyzed, appropriately diluted, is added to the immobilized phase. The preferred dilution rate is about 5-15%, preferably about 10%, by volume. Buffers that may be used for dilution for this purpose include (a) phosphate-buffered saline (PBS) containing 0.5% BSA, 0.05% TWEEN 20® detergent (P20), 0.05% PROCLIN® 300 antibiotic, 5 mM EDTA, 0.25% 3-((3-cholamidopropyl)dimethylammonio)-1-propanesulphonate (CHAPS) surfactant, 0.2% beta-gamma globulin, and 0.35M NaCl; (b) PBS containing 0.5% bovine serum albumin (BSA), 0.05% P20, and 0.05% PROCLIN® 300, pH 7; (c) PBS containing 0.5% BSA, 0.05% P20, 0.05% PROCLIN® 300, 5 mM EDTA, and 0.35 M NaCl, pH 6.35; (d) PBS containing 0.5% BSA, 0.05% P20, 0.05% PROCLIN® 300, 5 mM EDTA, 0.2% beta-gamma globulin, and 0.35 M NaCl; and (e) PBS containing 0.5% BSA, 0.05% P20, 0.05% PROCLIN® 300, 5 mM EDTA, 0.25% CHAPS, and 0.35 M NaCl. Buffer (a) is the preferred buffer for the assay herein since it has the best differentiation between each standard as well as the biggest signal-to-noise ratio. PROCLIN® 300 acts as a preservative, and TWEEN 20® acts as a detergent to eliminate non-specific binding. The added EDTA and salt of buffer (a) act to decrease the background over the other buffers, including buffer (b).

The amount of capture reagents employed is sufficiently large to give a good signal in comparison with the standards, but not in molar excess compared to the maximum expected level of antibody of interest in the sample. For sufficient sensitivity, it is preferred that the amount of biological sample added be such that the immobilized capture reagents are in molar excess of the maximum molar concentration of free antibody of interest anticipated in the biological sample after appropriate dilution of the sample. This anticipated level depends mainly on any known correlation between the concentration levels of the free antibody of interest in the particular biological sample being analyzed with the clinical condition of the patient. Thus, for example, an adult patient may have a maximum expected concentration of free antibody of interest in his/her serum that is quite high, whereas a child will be expected to have a lower level of free antibody of interest in his/her serum based on the doses given.

While the concentration of the capture reagents will generally be determined by the concentration range of interest of the antibody of interest, taking any necessary dilution of the biological sample into account, the final concentration of the capture reagents will normally be determined empirically to maximize the sensitivity of the assay over the range of interest. However, as a general guideline, the molar excess is suitably less than about ten-fold of the maximum expected molar concentration of antibody of interest in the biological sample after any appropriate dilution of the sample.

The conditions for incubation of sample and immobilized capture reagent are selected to maximize sensitivity of the assay and to minimize dissociation, and to ensure that any antibody of interest present in the sample binds to the immobilized capture reagent. Preferably, the incubation is accomplished at fairly constant temperatures, ranging from about 0° C. to about 40° C., preferably at or about room temperature. The time for incubation is generally no greater than about 10 hours. Preferably, the incubation time is from about 0.5 to 3 hours, and more preferably about 1.5-3 hours at or about room temperature to maximize binding of the antibody of interest to the capture reagents. The duration of incubation may be longer if a protease inhibitor is added to prevent proteases in the biological fluid from degrading the antibody of interest.

At this stage, the pH of the incubation mixture will ordinarily be in the range of about 4-9.5, preferably in the range of about 6-9, more preferably about 7 to 8. The pH of the incubation buffer is chosen to maintain a significant level of specific binding of the capture reagents to the antibody of interest being captured. Various buffers may be employed to achieve and maintain the desired pH during this step, including borate, phosphate, carbonate, TRIS—HCl or TRIS-phosphate, acetate, barbital, and the like. The particular buffer employed is not critical to the invention, but in individual assays one buffer may be preferred over another.

Optionally, the biological sample is separated (preferably by washing) from the immobilized capture reagents to remove uncaptured antibody of interest. The solution used for washing is generally a buffer ("washing buffer") with a pH determined using the considerations and buffers described above for the incubation step, with a preferable pH range of about 6-9. The washing may be done three or more times. The temperature of washing is generally from refrigerator to moderate temperatures, with a constant temperature maintained during the assay period, typically from about 0-40° C., more preferably about 4-30° C. For example, the wash buffer can be placed in ice at 4° C. in a reservoir before the washing, and a plate washer can be utilized for this step. A cross-linking agent or other suitable agent may also be added at this stage to allow the now-bound antibody of interest to be covalently attached to the capture reagents if there is any concern that the captured antibody of interest may dissociate to some extent in the subsequent steps.

The immobilized capture reagents with any bound antibody of interest present are contacted with detectable antibody, preferably at a temperature of about 20-40° C., more preferably about 36-38° C., with the exact temperature and time for contacting the two being dependent primarily on the detection means employed. For example, when 4-methylumbelliferyl-β-galactoside (MUG), streptavidin-HRP, or streptavidin-β-galactosidase is used as the means for detection, preferably the contacting is carried out overnight (e.g., about 15-17 hours or more) to amplify the signal to the maximum. While the detectable antibody may be a polyclonal or monoclonal antibody, preferably it is a monoclonal antibody that can be rodent, e.g., murine. In certain embodiments, the detectable antibody can be 11F12 or 13G4, in particular 13G4, to reduce background noise. Also, the preferred detectable antibody is directly detectable, and preferably is biotinylated. The detection means for the biotinylated label is preferably avidin or streptavidin-HRP, and the readout of the detection means is preferably fluorimetric or colorimetric.

A molar excess of an antibody with respect to the maximum concentration of free antibody of interest expected (as described above) is added to the plate after it is washed. This antibody (which is directly or indirectly detectable) is preferably a monoclonal antibody, although any antibody can be employed. The affinity of the antibody must be sufficiently high that small amounts of the free antibody of interest can be detected, but not so high that it causes the antibody of interest to be pulled from the capture reagents.

The same anti-idiotypic antibody can be used for coat and detection in the assay, or different antibodies can be used for coat and detection. They are preferably selected so that the background noise is minimized.

The level of any free antibody of interest from the sample that is now bound to the capture reagents is measured using a detection means for the detectable antibody. If the biological sample is from a clinical patient, the measuring step preferably comprises comparing the reaction that occurs as a result of the above steps with a standard curve to determine the level of antibody of interest compared to the known amount.

The antibody added to the immobilized capture reagents will be either directly labeled, or detected indirectly by addition, after washing off of excess first antibody, of a molar excess of a second, labeled antibody directed against IgG of the animal species of the first antibody. In the latter, indirect assay, labeled antisera against the first antibody are added to the sample so as to produce the labeled antibody in situ.

The label used for either the first or second antibody is any detectable functionality that does not interfere with the binding of free antibody of interest to the anti-idiotypic antibodies. Examples of suitable labels are those numerous labels known for use in immunoassay, including moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare-earth chelates or fluorescein and its derivatives, rhodamine and its derivatives, ruthenium, dansyl, umbelliferone, luceriferases, e.g., firefly luciferase and bacterial luciferase (U.S. Pat. No. 4,737,456), luciferin, 2,3-dihydrophthalazinediones, HRP, alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin (detectable by, e.g., avidin, streptavidin, streptavidin-HRP, and streptavidin-β-galactosidase with MUG), spin labels, bacteriophage labels, stable free radicals, and the like. The preferred label is biotin and the preferred detection means is avidin or streptavidin-HRP.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature* 144:945 (1962); David et al., *Biochemistry*, 13:1014-1021 (1974); Pain et al., *J. Immunol. Methods* 40:219-230 (1981); and Nygren, *J. Histochem. and Cytochem.*, 30:407-412 (1982). The most preferred label herein is biotin using streptavidin-HRP for detection means.

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147-166.

Following the addition of last labeled antibody, the amount of bound antibody is determined by removing excess unbound labeled antibody through washing and then measuring the amount of the attached label using a detection method appropriate to the label, and correlating the measured amount with the amount of the antibody of interest in the biological sample. For example, in the case of enzymes, the amount of color developed and measured will be a direct measurement of the amount of the antibody of interest present. Specifically, if HRP is the label, the color is detected using the substrate OPD at 490-nm absorbance.

In one example, after an enzyme-labeled second antibody directed against the first unlabeled antibody is washed from the immobilized phase, color or chemiluminiscence is developed and measured by incubating the immobilized capture reagent with a substrate of the enzyme. Then the concentration of the antibody of interest is calculated by comparing with the color or chemiluminescence generated by the standard antibody of interest run in parallel.

IV. Antibody Production

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor, using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2, P3X63Ag.U.1, or X63-Ag8-653 cells available from the American Type Culture Collection, Manassas, Va. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antibody of interest. Preferably, the binding specificity of monoclonal antibodies produced by hybridoma cells is determined by immunoprecipitation or by an in vitro binding assay, such as radioimmunoassay (RIA) or ELISA. Such clones are also screened for those that produce the least background noise in the assay when used as capture reagents and/or detectable antibodies The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-SEPHAROSE® agarose chromatography, hydroxylapatite chromatography, gel electrophoresis, dialysis, or affinity chromatography.

One specific preparation technique using hybridoma technology comprises immunizing mice such as CAF1 mice or Balb/c, for example, by injection in the footpads or spleen, with the antibody of interest in an adjuvant such as monophosphoryl lipid A/trehalose dicorynomycolate or as a conjugate of the antibody of interest with keyhole limpet haemocyanin (KLH) or with Limulus hemocyanin. Injections are done as many times as needed. The mice are sacrificed and popliteal lymph nodes or splenocytes obtained from the immunized mice, especially those with high titers, are fused with a murine myeloma cell line such as SP2/0 or P3X63Ag.U.1 (American Type Culture Collection (ATCC, Manassas, Va.)).

The resulting hybridomas are screened for antibodies with binding affinity for the antibody of interest but not other antibodies binding to a different antigen. This screening may take place by conventional ELISA for secretion of antibody that binds to immobilized antibody of interest or for production of IgG with an inhibition capacity of more than about 95% (inhibition of binding of the antibody of interest to the protein antigen). This screen defines a population of antibodies with nominal or higher reactivity as well as selectivity for the antibody of interest. Further selection may be performed to identify those antibodies with properties especially preferred for ELISAs. The criteria used for selecting a preferred anti-idiotypic antibody include that it should bind to the antibody of interest with relatively high affinity (Kd less than about $10^{-8}$M), and its binding to the antibody of interest should be mutually exclusive with binding to the analyte cytokine protein. It should also provide the cleanest assay with the least background noise.

The positive clones may be re-screened using surface plasmon resonance using a BIACORE® instrument to measure the affinity of the anti-idiotypic antibody for the antibody of interest (as reflected in its off-rate) and the mutual exclusivity of binding. Rabbit anti-mouse IgG(Fc) may be immobilized onto the biosensor surface and used to capture anti-idiotypic antibodies from hybridoma culture supernates. The antibody of interest at 0.2 nM alone and in the presence of 0.9 nM C-reactive protein (CRP) may be injected over the surface of the immobilized anti-idiotypic antibody and the relative mass accumulation compared. The hybridoma cells that are selected are cloned as by limiting dilution to obtain the desired clones. The anti-idiotypic antibody can then be purified and isolated from these clones. See U.S. Pub. No. US 20020142356 for an example of preparing an anti-idiotypic antibody, as well as Durrant et al., *Int J. Cancer*, 1:92(3):414-20 (2001) and Bhattacharya-Chatterjee, *Curr. Opin. Mol. Ther.*, 3(1):63-9 (2001).

The monoclonal antibodies may also be produced recombinantly. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plueckthun, *Immunol. Revs.*, 130: 151-188 (1992).

In a further embodiment, antibodies or antibody fragments can be isolated from antibody phage libraries generated using the techniques described in McCafferty et al., *Nature*, 348: 552-554 (1990). Clackson et al., Nature, 352:624-628 (1991) and Marks et al., *J. Mol. Biol.*, 222:581-597 (1991) describe the isolation of murine and human antibodies, respectively, using phage libraries. Subsequent publications describe the production of high-affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin-coding sequence all or part of the coding sequence for a non-immunoglobulin polypeptide.

Many of the procedures useful for practicing the present invention, whether or not described herein in detail, are well known to those skilled in the arts of molecular biology, biochemistry, immunology, and medicine. Once the antibody of interest is identified, generating the anti-idiotypic antibody would be within the skill of the ordinarily skilled practitioner in this field.

V. Kits

The assay method of this invention can be provided in the form of a kit. Such a kit is a packaged combination including the basic elements of:

(a) capture reagents comprised of anti-idiotypic antibodies against the antibody of interest, wherein the antibodies bind specifically to two different binding sites on the antibody of interest;

(b) detectable (labeled or unlabeled) anti-idiotypic antibodies that bind specifically to two different binding sites on the antibody of interest; and (c) instructions on how to perform the assay method using these reagents.

Preferably, the kit further comprises a solid support for the capture reagents, which may be provided as a separate element or on which the capture reagents are already immobilized. Hence, the capture antibodies in the kit may be immobilized on a solid support, or they may be immobilized on such support that is included with the kit or provided separately from the kit. Preferably, the capture reagents are coated on a microtiter plate. The detectable antibodies may be labeled antibodies detected directly or unlabeled antibodies that are detected by labeled antibodies directed against the unlabeled antibodies raised in a different species. Where the label is an enzyme, the kit will ordinarily include substrates and cofactors required by the enzyme, where the label is a fluorophore, a dye precursor that provides the detectable chromophore, and where the label is biotin, an avidin such as avidin, streptavidin, or streptavidin conjugated to HRP or 0-galactosidase with MUG.

In a specific embodiment, the capture reagents are monoclonal antibodies, which can be rodent (murine or rat), e.g., 11F12 or 13G4, as described herein Also in certain embodiments, the detectable antibody is a biotinylated monoclonal antibody, which can be rodent (murine or rat), e.g., 11F12 or 13G4. The capture reagents are immobilized in this kit.

The kit also typically contains the antibody of interest as a standard (e.g., purified antibody of interest), as well as other additives such as stabilizers, washing and incubation buffers, and the like.

Examples of standards for the antibody of interest are monoclonal antibodies, more preferably humanized antibodies, and still more preferably a humanized 12G8 antibody.

The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

All references cited herein are incorporated herein by reference to the same extent as if each individual publication, patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

EXAMPLES

I. Immunizations and Antibody Selection

Immunizations were performed using 10 Balb/c mice and humanized 12G8 anti-IL-10 Fab as immunogen with MPL+ TDM (Sigma) as adjuvant. Initially, all mice were immunized with 10 µg Fab in 50 µL; subsequent dosings were every 8 days with 5 µg in 50 µL; all doses were administered via the right leg footpad. One week after the sixth dosing, a fusion was performed using lymph nodes. Hybridoma supernatents were screened using a primary screen sandwich-ELISA format followed by a secondary screen blocking-ELISA format (described below). The primary screen gave 127 antibodies that bound to humanized 12G8 Fab and the secondary screen showed that 29 of the 127 blocked interaction of humanized 12G8 with human IL-10. Of these blocking antibodies, 5 were subcloned.

For the sandwich-ELISA format, 96-well plates were coated at 4° C. overnight with 100 µL/well of goat anti-mouse IgG Fc (stock 1 µg/mL). Plates were then washed three times with phosphate-buffered saline (PBS)-0.05% Tween 20. Hybridomas supernatents (50 µL) were added to a well. After incubation at 25° C. for 1 hr, plates were washed three times. A stock solution of biotinylated humanized 12G8 Fab (250 ng/mL in PBS-0.1% BSA-0.05% Tween 20) was added to each well at 100 μL/well. After 45 min incubation, plates were washed three times. Streptavidin-HRP (1:2000 dilution in PBS-0.1% BSA-0.05% Tween 20) was added to 100 μL/well. After 45 min incubation, plates were washed three times. Substrate ABTS was added at 100 μL/well. After incubation for 10 min, absorbance at 405 nm was read.

For the blocking ELISA, 96-well plates were coated at 4° C. overnight with 50 μL/well of human IL-10 (stock 500 ng/mL) (Plate #1). In a separate V-bottom 96-well plate (Plate #2), hybridoma supernatents (60 μL/well) were incubated with 60 μL/well of 500 ng/mL biotinylated humanized 12G8 at 25° C. for 30 min. Plate #1 was washed three times with PBS-0.05% Tween 20. Then from each well on plate #2, 100 μL of the pre-incubated humanized 12G8 was transferred to plate #1. After 1 hr incubation at 25° C., plate #1 was washed three times and 100 μL/well streptavidin-HRP (1:2000 dilution in PBS-0.1% BSA-0.05% Tween 20) was added and incubated at 25° C. for 45 min. 100 μL/well ABTS substrate was incubated at 25° C. for 10 min and absorbance read at 405 nm. For purified antibodies, 2 μg/mL with 1:3 dilutions were titrated across the plate.

The anti-idiotypic antibodies were selected that bound humanized 12G8 antibody fragments (Fab and scFv forms), but not bind to human IgG, and did not block binding of humanized 12G8 to human IL-10.

TABLE 1

IC50 of humanized 12G8 anti-idiotypic antibodies

| mAb | subclass | IC50(nM) |
| --- | --- | --- |
| JL11.11F12 | IgG2b/k | 2.0 |
| JL11.13G4 | IgG1/k | 1.0 |
| JL11.14E4 | IgG2b/k | 1.8 |
| JL11.26F1 | IgG1/k | 1.6 |
| JL11.2F7 | IgG1/k | 0.8 |
| Humanized 12G8 | | 1.7 |

II. Antibody Selection and Titration

Antibody pair selection was performed using an ELISA format. The above described anti-idiotypic antibodies. 13G4 and 2F7, selected as capture antibodies, were diluted to 0.5, 1 and 2 μg/mL in PBS and coated onto microtiter plates overnight. The following day, the contents was aspirated and unbound sites were blocked for at least 30 minutes using 1% BSA dissolved in PBS with 0.05% sodium azide. Plates were washed and used or alternatively, stored refrigerated until use. Humanized 12G8, diluted to 100, 1, and 0.1 ng/mL in PBS conting 20% cynomologus monkey serum, was incubated with the capture antibodies for two hours at room temperature. The plates were washed four times using EIA Wash Buffer (PBS with 0.1% Tween 20). Anti-idiotypic antibodies 11F12 and 14E4 were biotinylated as described below, and diluted to 0.5, 1 and 2 μg/mL. The biotinylated antibodies were added to the wells and incubated for 45 minutes at room temperature. The plates were washed as previously described. Horesradish peroxidase (HRP) conjugated streptavidin (Kirekegaard & Perry Laboratories, Giethersburg, Md.), diluted to 0.25 μg/mL in 0.1% BSA/PBS was added and incubated for 45 minutes at room temperature. The plates were washed a final time as described above. Tetramethylbenzidine was added and reacted with the bound HRP to form a colorimetric reaction. The colored product was measured spectrophotometrically. Mean optical density (OD) was used to determine signal to noise ratios.

TABLE 2

Signal to noise ratio of 13G4 (capture) and 11F12 (detection) anti-idiotypic antibodies to detect humanized 12G8 (100 ng/mL)

| Concentration of 13G4 (μg/mL) | Concentration of 11F12 (μg/mL) | Signal:Noise Ratio |
| --- | --- | --- |
| 0.5 | 0.5 | 10.0 |
| 0.5 | 1.0 | 8.0 |
| 0.5 | 2.0 | 8.0 |
| 1.0 | 0.5 | 32.0 |
| 1.0 | 1.0 | 40.0 |
| 1.0 | 2.0 | 25.0 |
| 2.0 | 0.5 | 22.0 |
| 2.0 | 1.0 | 7.5 |
| 2.0 | 2.0 | 20.0 |

TABLE 3

Signal to noise ratio of 13G4 (capture) and 14E4 (detection) anti-idiotypic antibodies to detecthumanized 12G8 (100 ng/mL)

| Concentration of 13G4 (μg/mL) | Concentration of 14E4 (μg/mL) | Signal:Noise Ratio |
| --- | --- | --- |
| 0.5 | 0.5 | 8.0 |
| 0.5 | 1.0 | 4.0 |
| 0.5 | 2.0 | 10.0 |
| 1.0 | 0.5 | 22.5 |
| 1.0 | 1.0 | 12.5 |
| 1.0 | 2.0 | 17.0 |
| 2.0 | 0.5 | 34.0 |
| 2.0 | 1.0 | 17.5 |
| 2.0 | 2.0 | 24.5 |

TABLE 4

Signal to noise ratio of 13G4 (capture) and 2F7 (detection) anti-idiotypic antibodies to detecthumanized 12G8 (100 ng/mL)

| Concentration of 13G4 (μg/mL) | Concentration of 2F7 (μg/mL) | Signal:Noise Ratio |
| --- | --- | --- |
| 0.5 | 0.5 | 8.5 |
| 0.5 | 1.0 | 8.0 |
| 0.5 | 2.0 | 15.0 |
| 1.0 | 0.5 | 32.0 |
| 1.0 | 1.0 | 24.5 |
| 1.0 | 2.0 | 21.0 |
| 2.0 | 0.5 | 9.5 |
| 2.0 | 1.0 | 5.0 |
| 2.0 | 2.0 | 9.5 |

The antibody pair chosen was 13G4 and 11F12 based upon the high signal to noise ratio (40). All subsequent assays were performed with this pair of antibodies. For ELISA based assays, the antibodies were used at a concentration of 1 μg/mL.

III. Coupling of Anti-Idiotypic Antibodies to Biotin and Ruthenium

Monoclonal anti-idiotypic antibodies JL11.11F12.C4 (11F12) and JL11.13G4.B11 (13G4) were each diluted to 1 mg/mL in Dulbeccos' phosphate-buffered saline, pH 7.8. Using procedures supplied by BioVeris (Gaithersburg, Md.), biotin-LC-Sulfo-NHS-ester was coupled to 11F12 at a 20:1 coupling ratio, whereas ruthenium (II) tris-bipyridine, N-hydroxysuccinimide (BV-TAG) was coupled to 13G4 at a coupling ratio of 8:1. Both the N-hydroxysulfo-succinimide (NHS) ester of biotin and the BV-TAG couple to primary amine groups on 11F12 and 13G4 during a 60 minute incubation at room temperature while shaking Unbound biotin or BV-TAG was separated from bound conjugate using dialysis. An equal volume of 3% (w/v) bovine serum albumin in PBS, pH 7.3, was added to the coupled antibody.

IV. Anti-Idiotypic Antibody ECL Immunoassay for Measuring Serum Concentrations of Humanized Anti-IL-10 12G8 Antibody For measuring serum concentrations of humanized anti-IL-10 IgG for pre-clinical studies, an electrochemiluminescent (ECL) immunoassay was developed using specific anti-idiotypic antibodies to the humanized anti-IL-10 antibody, 12G8. The antibodies 11F12, which was biotinylated (biotin-11F12), and 13G4, which was ruthenylated (TAG-13G4), bind to different idiotopes on the humanized anti-IL-10 antibody. Humanized anti-IL-10 IgG (7.0-900 ng/mL in 2-fold serial dilutions) in cynomolgus monkey serum was added to 96-well polypropylene microplates (Costar, Cambridge, Mass.) along with the coupled antibodies diluted in Dulbeccos' phosphate-buffered saline (PBS), pH 7.4, with 1% (w/v) bovine serum albumin and 1% (v/v) mouse serum.

After 2 hours at room temperature, during which time a sandwich complex was formed between anti-IL-10 antibody in the sample and the anti-idiotypic antibodies, streptavidin-coated M280 Dynabeads (BioVeris), diluted to 0.6 mg/mL, was added and incubated for 30-60 minutes at room temperature. Diluent was added to bring the total volume in the wells to 250 µL. Plates were read on the BioVeris M-384 plate reader. A magnet in the instrument captures the beads, bound to the antibody complex, on the surface of an electrode. This occurs in a flow cell, effectively separating the complex from unbound labels and other components in the matrix. Applying voltage to the electrode excites the TAG-13G4 near the surface of the electrode, resulting in luminescence which is captured on a photodetector and is proportional to the amount of anti-IL-10 antibody in the sample.

The titration curves of standard were fitted with a log-log regression curve-fitting program (SOFTmax PRO, Molecular Devices Corp, Sunnyvale, Calif.). The recovery of 9-900 ng/mL humanized anti-IL-10 IgG in cynomolgus monkey serum was 98-105%, whereas the intra- and inter-assay coefficient of variation (CVs) were 4.9% and 6.5%, respectively. With a sensitivity of 9 ng/mL for humanized anti-IL-10 IgG in cynomolgus monkey serum, this assay can be used to support pre-clinical studies.

V. Development of ELISA-based Assay

The anti-idiotypic antibodies 11F12 and 13G4 were also to develop an ELISA. High binding 96-well microtiter plates (Costar) were coated overnight at 4° C. with 1.0 µg/mL anti-idiotypic antibody 11F12 in 50 mM carbonate/bicarbonate buffer (Sigma) Plates were blocked with 1% (w/v) bovine serum albumin, 0.05% (v/v) Tween® 20 non-ionic surfactant in PBS. Humanized 12G8 (0.938-120 ng/mL in 2-fold serial dilutions) in 25% human serum or 25% human urine were added to the plates.

After a 1 hour incubation at 25° C., antibody bound to the plates was detected by adding biotinylated 13G4 followed by HRP conjugated to NeutrAvidin (Pierce, Rockford, Ill.). Plates were developed using the substrate 3,3',5,5'-tetramethyl benzidine (KPL). The reaction was stopped using 85% o-phosphoric acid (EMD). Absorbance was read at 450 nm on an Emax plate reader (Molecular Devices Corp, Sunnyvale, Calif.).

The titration curves of standard were fitted with a four-parameter regression curve-fitting program (SOFTmax PRO, Molecular Devices Corp, Sunnyvale, Calif.). The back-calculated concentrations of 1.875-120 ng/mL of the humanized anti-IL-10 IgG standards in 25% human serum were 94-100% of nominal and in 25% urine were 91-100% of nominal. Inter-assay CVs in serum and urine were 7.7% and 10.1%, respectively. This assay, therefore, has a sensitivity to detect 7.5 ng/mL of humanized 12G8 in both human serum and human urine and can be used to support clinical studies.

All references cited herein are incorporated herein by reference to the same extent as if each individual publication, patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An assay method for specifically detecting in a plasma or serum sample, a humanized 12G8 antibody that binds to mammalian IL-10 comprising
   (a) contacting and incubating the sample with a first idiotypic capture antibody selected from the group consisting of 11F12 and 13G4, which binds to the humanized 12G8 antibody but not any other antibody in the sample that binds to mammalian IL-10;
   (b) contacting the sample, and hence any bound humanized 12G8 antibody, with a second idiotypic detection antibody selected from the group consisting of 11F12 and 13G4 which binds to the humanized 12G8 antibody but not any other antibody in the sample that binds to mammalian IL-10;
   (c) measuring the level of any of the humanized 12G8 antibody bound; and
   d) determining the level of humanized 12G8 antibody in the plasma or serum sample using a standard titration curve.

2. The method of claim 1 wherein the plasma or serum is isolated from a primate subject.

3. The method of claim 2 wherein the primate is a cynomologous monkey.

4. The method of claim 2, wherein the primate is a human.

5. The method of claim 1 wherein the measuring further comprises using a standard curve to determine the level of the humanized 12G8 antibody compared to a known level.

6. The method of claim 1 wherein the mammalian IL-10 is primate IL-10.

7. The method of claim 6, wherein the primate IL-10 is cynomologous monkey IL-10.

8. The method of claim 6, wherein the primate IL-10 is human IL-10.

9. The method of claim 1 wherein the first and second idiotypic antibodies are monoclonal antibodies.

10. The method of claim 1 wherein the first and second idiotypic antibodies are murine antibodies.

11. The method of claim 1 wherein the first idiotypic antibody is a capture reagent selected from the group consisting of 11F12 and 13G4 wherein:
   a) 11F12 comprises a variable heavy chain of SEQ ID NO: 1 and a variable light chain of SEQ ID NO: 2; and
   b) 13G4 comprises a variable heavy chain of SEQ ID NO: 3 and a variable light chain of SEQ ID NO: 4.

12. The method of claim 1, wherein the assay is an electrochemiluminescence (ECL) immunoassay and 11F12 is a capture antibody and 13G4 is a detection antibody.

13. The method of claim 12, wherein 11F12 is conjugated to biotin and 13G4 is conjugated to ruthenium.

14. The method of claim 1, wherein the assay is an enzyme-linked immunosorbent assay (ELISA) and 13G4 is a capture antibody and 11F12 is a detection antibody.

15. The method of claim 14, wherein the 11F12 is conjugated to biotin.

16. The method of claim 1 wherein the second idiotypic antibody is a detectable antibody selected from the group consisting of 11F12 and 13G4 wherein:
   a) 11F12 comprises a variable heavy chain of SEQ ID NO: 1 and a variable light chain of SEQ ID NO: 2; and
   b) 13G4 comprises a variable heavy chain of SEQ ID NO: 3 and a variable light chain of SEQ ID NO: 4.

* * * * *